(12) United States Patent
Lu et al.

(10) Patent No.: US 11,578,576 B2
(45) Date of Patent: Feb. 14, 2023

(54) METHOD FOR CHARACTERIZING COMPLEXITY OF ROCK FRACTURE BASED ON FRACTAL DIMENSION AND DEVICE THEREOF

(71) Applicant: Southwest Petroleum University, Chengdu (CN)

(72) Inventors: Cong Lu, Chengdu (CN); Jianchun Guo, Chengdu (CN); Junfeng Li, Chengdu (CN); Yunchuan Zheng, Chengdu (CN); Congbin Yin, Chengdu (CN); Meiping Li, Chengdu (CN); Mingzhong Chen, Chengdu (CN); Zhihong Zhao, Chengdu (CN); Kun Wang, Chengdu (CN); Chi Chen, Chengdu (CN); Chuhao Huang, Chengdu (CN); Li Ma, Chengdu (CN); Fenglan Huang, Chengdu (CN); Ye Zhong, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 700 days.

(21) Appl. No.: 16/550,166

(22) Filed: Aug. 23, 2019

(65) Prior Publication Data
US 2020/0240251 A1    Jul. 30, 2020

(30) Foreign Application Priority Data
Jan. 28, 2019 (CN) .......................... 201910081165.9

(51) Int. Cl.
*E21B 43/26* (2006.01)
*G01V 1/50* (2006.01)
(Continued)

(52) U.S. Cl.
CPC .............. *E21B 43/26* (2013.01); *E21B 49/00* (2013.01); *G01N 33/24* (2013.01); *G01V 1/50* (2013.01); *G01V 2210/646* (2013.01)

(58) Field of Classification Search
CPC ................................. E21B 43/26; E21B 49/00
(Continued)

(56) References Cited

U.S. PATENT DOCUMENTS

| 2015/0218925 A1* | 8/2015 | Lecampion | ............. E21B 43/11 166/297 |
| 2018/0016897 A1* | 1/2018 | Willberg | ................. E21B 41/00 |

(Continued)

*Primary Examiner* — William D Hutton, Jr.
*Assistant Examiner* — Ashish K Varma

(57) ABSTRACT

A method for characterizing complexity of rock fracture based on fractal dimension and a device thereof are provided. The method includes steps of: collecting rock fracture samples of a rock, and collecting basic parameters of the rock; determining a fractal dimension of a rock fracture morphology of the rock; calculating the fractal dimension of the rock; calculating a complexity coefficient Fc of rock fracture of the rock; and characterizing a complexity of rock fracture of the rock based on the complexity coefficient Fc of rock fracture of the rock. In the present invention, combined with the fractal geometry theory, fracture complexity coefficient of shale rocks is redefined and calculated to accurately characterize rock fracture morphology, so that characteristics of rock fracture morphology is correctly understood and affecting factors of fracture morphology is analyzed.

6 Claims, 3 Drawing Sheets

(51) Int. Cl.
E21B 49/00 (2006.01)
G01N 33/24 (2006.01)

(58) Field of Classification Search
USPC .................................................... 166/250.1
See application file for complete search history.

(56) References Cited

U.S. PATENT DOCUMENTS

2018/0364381 A1* 12/2018 Raterman .............. G01V 9/005
2019/0145251 A1* 5/2019 Johnson ................ E21B 43/267
166/250.1

* cited by examiner

METHOD FOR CHARACTERIZING COMPLEXITY OF ROCK FRACTURE BASED ON FRACTAL DIMENSION AND DEVICE THEREOF

FIELD OF THE INVENTION

The present invention relates to the technique field of hydraulic fracturing, and more particularly to a method for characterizing complexity of rock fracture based on fractal dimension and a device thereof.

BACKGROUND OF THE INVENTION

The fracture of shale rocks is generally divided into three failure/fracture modes, namely, tensile splitting failure, multi-slit shear failure and single-slit shear failure. However, this division of sub-categories of fracture modes is relatively simple and may not accurately reflect the true fracture morphology of rocks, because the rock fracture morphology is not a single mode of absolute tensile splitting or single-slit shearing, but a complex fracture morphology with multiple fracture modes, and further because the complexity of rock fracture is different under different degrees of single fracture mode.

Therefore, it is necessary to accurately characterize the rock fracture morphology in order to correctly understand the characteristics of the rock fracture morphology and analyze the affecting factors of the fracture morphology.

It should be noted that the above description of the technical background is merely for the purpose of facilitating a clear and complete description of technical solutions of the present invention, and is convenient for understanding by those skilled in the art. The above technical solutions should not be considered to be well-known to those skilled in the art, simply because these aspects are set forth in background section of the present invention.

SUMMARY OF THE INVENTION

In order to solve the above problems in the prior art, it is an object of the present invention to provide a method for characterizing complexity of rock fracture based on fractal dimension.

According to an exemplary embodiment, a method for characterizing complexity of rock fracture based on fractal dimension is provided.

The method includes the following steps: (1) step A: collecting rock fracture samples of a rock, and collecting basic parameters of the rock; (2) step B: determining a fractal dimension of a rock fracture morphology of the rock; (3) step C: calculating the fractal dimension of the rock by the following formula (1):

$$N(R) = \frac{C}{R^D};$$

wherein N (R) is a number of square boxes containing slits; R is a side length; D is the fractal dimension; and C is a proportional constant; (4) step D: calculating a complexity coefficient Fc of rock fracture of the rock based on the fractal dimension D calculated from above formula and the following formula (2):

$$F_c = D \cdot \left(1 - \frac{\alpha}{90}\right);$$

wherein Fc is the complexity coefficient of rock fracture; α is a fracture angle of the rock; and (5) step E: characterizing a complexity of rock fracture of the rock based on the complexity coefficient Fc of rock fracture of the rock.

In one embodiment, the basic parameters in the step A comprise the fracture angle of the rock, Poisson's ratio, Young's modulus, peak strain, and peak stress.

In one embodiment, the step B further includes: (2-1) placing an end surface where the rock fracture is located within a square area of a certain length, and dividing the square area into a plurality of boxes with a side length R; and (2-2) calculating the number of the square boxes N (R) containing slits in different cases by adjusting the value of the side length R.

In one embodiment, when Fc>1.2, the complexity of rock fracture of the rock is characterized as a composite failure mode; when 1.2>Fc>1, the complexity of rock fracture of the rock is characterized as a tensile splitting mode; and when 1>Fc, the complexity of rock fracture of the rock is characterized as a shear failure mode.

According to another exemplary embodiment, a device for characterizing complexity of rock fracture based on fractal dimension is provided. The device includes a collection module, a determination module, a fractal dimension calculation module, a complexity coefficient calculation module, and a complexity characterization module. The collection module is configured to collect rock fracture samples of a rock, and collect basic parameters of the rock. The determination module is configured to determine a fractal dimension of a rock fracture morphology of the rock. The fractal dimension calculation module is configured to calculate the fractal dimension of the rock by the following formula (3):

$$N(R) = \frac{C}{R^D};$$

wherein N (R) is a number of square boxes containing slits; R is a side length; D is the fractal dimension; and C is a proportional constant. The complexity coefficient calculation module is configured to calculate a complexity coefficient Fc of rock fracture of the rock based on the fractal dimension D calculated from above formula and the following formula (4):

$$F_c = D \cdot \left(1 - \frac{\alpha}{90}\right);$$

wherein Fc is the complexity coefficient of rock fracture; α is a fracture angle of the rock. The complexity characterization module is configured to characterize a complexity of rock fracture of the rock based on the complexity coefficient Fc of rock fracture of the rock.

In one embodiment, the basic parameters comprise the fracture angle of the rock, Poisson's ratio, Young's modulus, peak strain, and peak stress.

In one embodiment, the determination module is further configured to: place an end surface where the rock fracture is located within a square area of a certain length, and divide the square area into a plurality of boxes with a side length R; and calculate the number of the square boxes N (R) containing slits in different cases by adjusting a value of the side length R.

In one embodiment, when Fc>1.2, the complexity characterization module is configured to characterize the complexity of rock fracture of the rock as a composite failure mode; when 1.2>Fc>1, the complexity characterization module is configured to characterize the complexity of rock fracture of the rock as a tensile splitting mode; and when 1>Fc, the complexity characterization module is configured to characterize the complexity of rock fracture of the rock as a shear failure mode.

The beneficial effects of the present invention are as follows: in the present invention, combined with the fractal geometry theory, the fracture complexity coefficient of shale rocks is redefined and calculated to accurately characterize the rock fracture morphology, so that the characteristics of rock fracture morphology may be correctly understood and the affecting factors of fracture morphology may be analyzed.

BRIEF DESCRIPTION OF THE DRAWINGS

Aspects of the present invention are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE PREFERRED EMBODIMENTS

Figure 1:
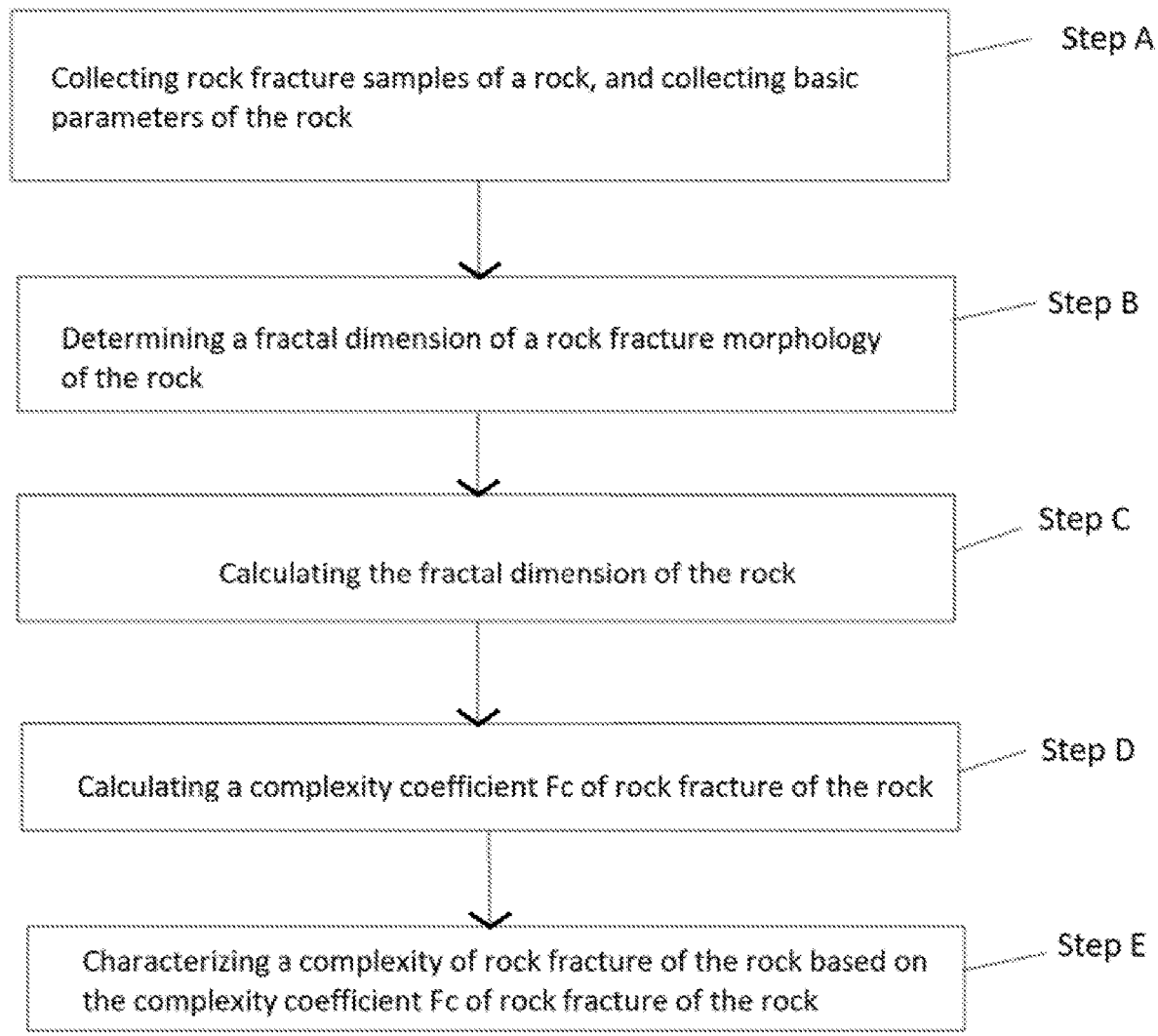
FIG. 1 is a flowchart of a method for characterizing complexity of rock fracture based on fractal dimension according to an embodiment of the present invention.

The following invention provides many different embodiments, or examples, for implementing different features of the provided subject matter. Specific examples of components and arrangements are described below to simplify the present invention. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present invention may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Please refer to FIG. 1. FIG. 1 is a flowchart of a method for characterizing complexity of rock fracture based on fractal dimension according to an embodiment of the present invention. As shown in FIG. 1, the method for characterizing complexity of rock fractures based on fractal dimension includes the following steps.

(1) Step A: collecting rock fracture samples of a rock, and collecting basic parameters of the rock.

In a specific implementation of the present invention, the basic parameters may include the fracture angle of the rock, Poisson's ratio, Young's modulus, peak strain, and peak stress. However, this is merely an example and should not be a limitation of the present invention.

(2) Step B: determining a fractal dimension of a rock fracture morphology of the rock.

In a specific implementation of the present invention, a box method is used for determining the fractal dimension of the rock fracture morphology of the rock. First, an end surface of the rock where the rock fracture is located is placed within a square area of a certain length, and the square area is divided into a plurality of boxes with a side length R. The number of the square boxes N(R) containing slits in different cases is calculated by adjusting the value of the side length R.

(3) Step C: calculating the fractal dimension of the rock by the following formula (1):

$$N(R) = \frac{C}{R^D};\quad(1)$$

wherein N(R) is a number of square boxes containing slits; R is a side length; D is the fractal dimension; and C is a proportional constant.

(4) Step D: calculating a complexity coefficient Fc of rock fracture of the rock based on the fractal dimension D calculated from above formula (1) and the following formula (2):

$$F_C = D \cdot \left(1 - \frac{\alpha}{90}\right);\quad(2)$$

wherein Fc is the complexity coefficient of rock fracture; α is a fracture angle of the rock.

(5) Step E: characterizing a complexity of rock fracture of the rock based on the complexity coefficient Fc of rock fracture of the rock.

For example, when Fc>1.2, the complexity of rock fracture of the rock is characterized as a composite failure mode; when 1.2>Fc>1, the complexity of rock fracture of the rock is characterized as a tensile splitting mode; and when 1>Fc, the complexity of rock fracture of the rock is characterized as a shear failure mode. However, this is merely an example and should not be a limitation of the present invention.

Figure 2:
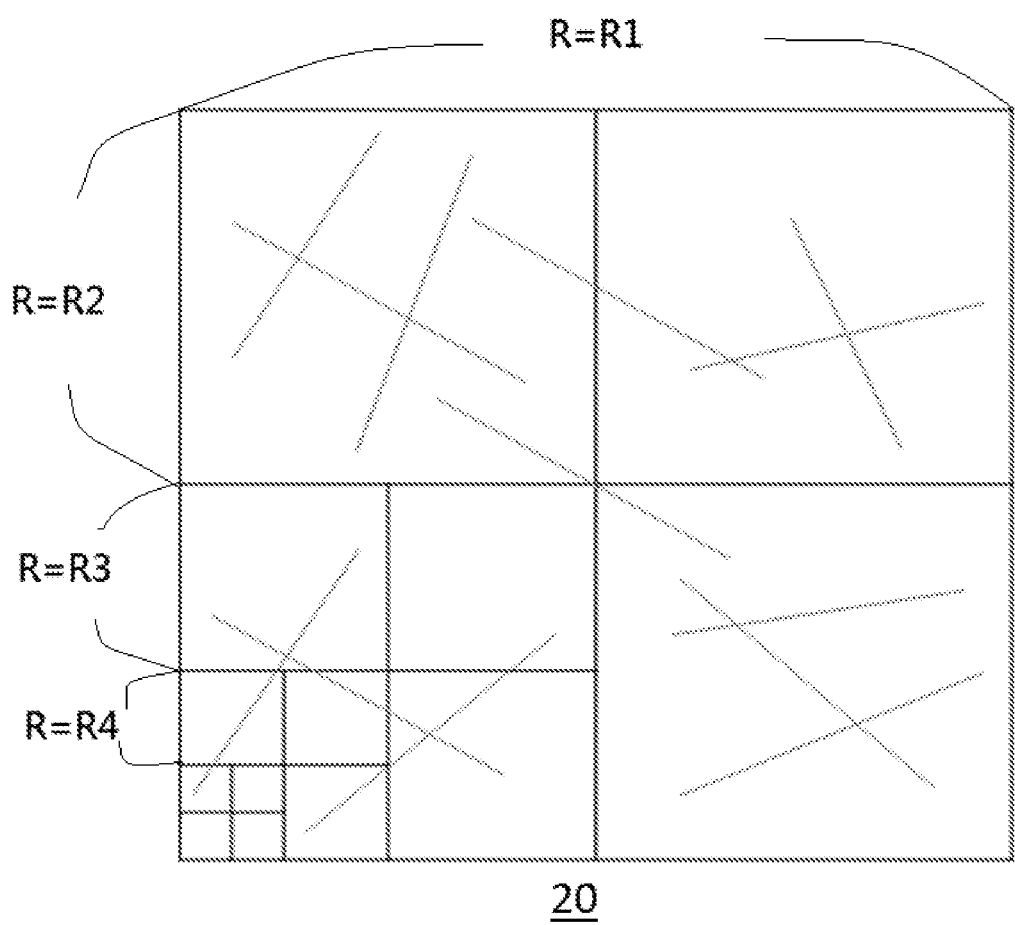
FIG. 2 is a schematic diagram for calculating fractal dimensions using a box method according to an embodiment of the present invention.

Please refer to FIG. 2.

FIG. 2 is a schematic diagram for calculating fractal dimensions using a box method according to an embodiment of the present invention.

As shown in FIG. 2, a square area 20 of a length R=R1 is provided. First, the end surface of the rock having slits where the rock fracture is located is placed within the square area 20. After that, the number of the boxes N (R) containing slits in different cases is calculated by adjusting a value of the side length R. The square area 20 is divided into four boxes with a side length R=R2, where R2=R1/2. For example, when R=R2, the number of boxes N(R) is equal to 4; when R=R3, where R3=R1/4, the number of boxes N(R) is equal to 16; when R=R4, where R4=R1/8, the number of boxes N(R) is equal to 64; and so on.

Be noted that, when R=R1, the fractal dimension D of the rock is 1; when R=R2=R1/2, the fractal dimension D of the rock is 2; when R=R3=R1/4, the fractal dimension D of the rock is 3; when R=R4=R1/8, the fractal dimension D of the rock is 4; and so on.

Figure 3:
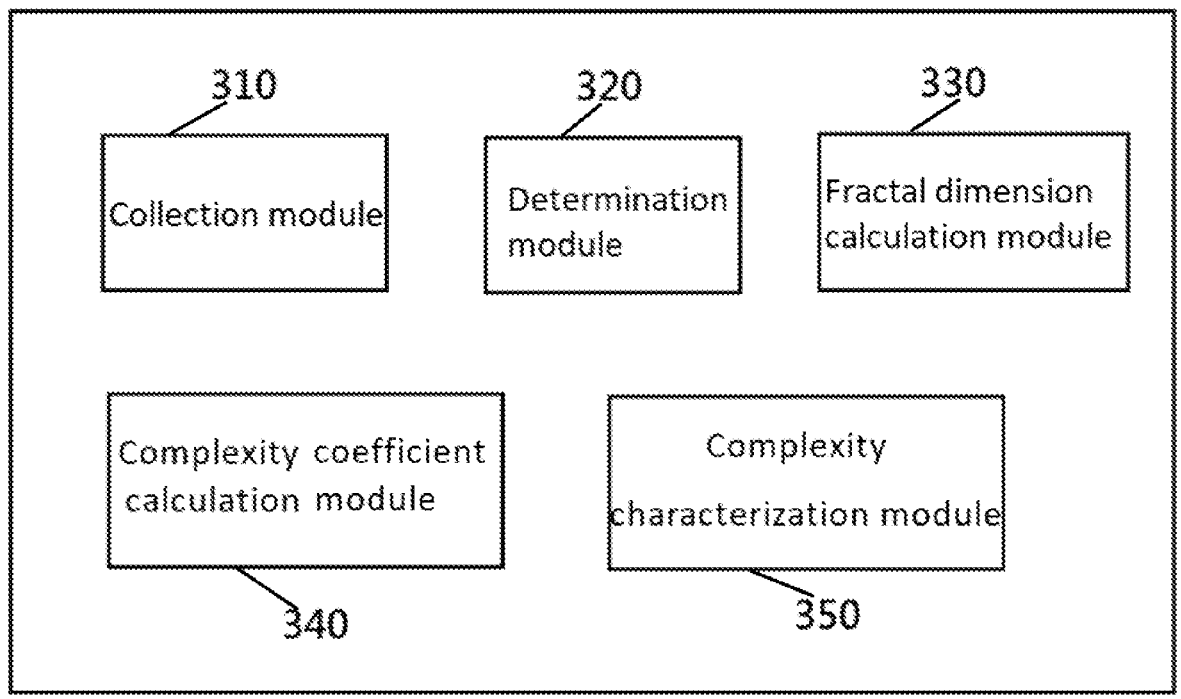
FIG. 3 is a block diagram of a device for characterizing complexity of rock fracture based on fractal dimension according to an embodiment of the present invention.

FIG. 3 is a block diagram of a device 30 for characterizing complexity of rock fracture based on fractal dimension according to an embodiment of the present invention. As shown in FIG. 3, the device 30 includes a collection module 310, a determination module 320, a fractal dimension calculation module 330, a complexity coefficient calculation module 340, and a complexity characterization module 350. The collection module 310 is configured to collect rock fracture samples of a rock, and collect basic parameters of the rock. The determination module 320 is configured to determine a fractal dimension of a rock fracture morphology of the rock. The fractal dimension calculation module 330 is configured to calculate the fractal dimension of the rock by the following formula (3):

$$N(R) = \frac{C}{R^D}; \quad (3)$$

wherein N(R) is a number of square boxes containing slits; R is a side length; D is the fractal dimension; and C is a proportional constant. The complexity coefficient calculation module 340 is configured to calculate a complexity coefficient Fc of rock fracture of the rock based on the fractal dimension D calculated from above formula (3) and the following formula (4):

$$F_C = D \cdot \left(1 - \frac{\alpha}{90}\right); \quad (4)$$

wherein Fc is the complexity coefficient of rock fracture; and α is a fracture angle of the rock. The complexity characterization module 350 is configured to characterize a complexity of rock fracture of the rock based on the complexity coefficient Fc of rock fracture of the rock.

In a specific implementation of the present invention, the basic parameters may include the fracture angle of the rock, Poisson's ratio, Young's modulus, peak strain, and peak stress. However, this is merely an example and should not be a limitation of the present invention.

In a specific implementation of the present invention, the determination module 320 is further configured to place an end surface of the rock where the rock fracture is located within a square area of a certain length, and divide the square area into a plurality of boxes with a side length R; and calculate the number of the square boxes N(R) containing slits in different cases by adjusting a value of the side length R.

Be noted that, a box method is used by the determination module 320 for determining the fractal dimension of the rock fracture morphology of the rock.

In a specific implementation of the present invention, when Fc>1.2, the complexity characterization module 350 is configured to characterize the complexity of rock fracture of the rock as a composite failure mode; when 1.2>Fc>1, the complexity characterization module 350 is configured to characterize the complexity of rock fracture of the rock as a tensile splitting mode; and when 1>Fc, the complexity characterization module 350 is configured to characterize the complexity of rock fracture of the rock as a shear failure mode. However, this is merely an example and should not be a limitation of the present invention.

The beneficial effects of the present invention are as follows: in the present invention, combined with the fractal geometry theory, the fracture complexity coefficient of shale rocks is redefined and calculated to accurately characterize the rock fracture morphology, so that the characteristics of rock fracture morphology may be correctly understood and the affecting factors of fracture morphology may be analyzed.

By adopting the method for characterizing complexity of rock fracture based on fractal dimension and the device thereof of the present invention, the development of gas (oil) reservoir layers of shale rocks can be improved, and the reach range of production wells and the permeability of gas (oil) reservoir layers can be increased. Therefore, gas (oil) production of shale rocks can be improved, and production costs can be reduced, so as to achieve commercial scale development.

The foregoing outlines features of several embodiments so that those skilled in the art may better understand the aspects of the present invention. Those skilled in the art should appreciate that they may readily use the present invention as a basis for designing or modifying other processes and structures for carrying out the same purposes and/or achieving the same advantages of the embodiments introduced herein. Those skilled in the art should also realize that such equivalent constructions do not depart from the spirit and scope of the present invention, and that they may make various changes, substitutions, and alterations herein without departing from the spirit and scope of the present invention.

What is claimed is:

1. A method for characterizing complexity of rock fracture based on fractal dimension, comprising:
   step A: collecting rock fracture samples of a rock, and collecting basic parameters of the rock;
   step B: determining a fractal dimension of a rock fracture morphology of the rock;
   step C: calculating the fractal dimension of the rock by formula (1) as follow:

$$N(R) = \frac{C}{R^D}; \quad (1)$$

wherein N(R) is a number of square boxes containing slits; R is a side length; D is the fractal dimension; and C is a proportional constant;
   step D: calculating a complexity coefficient Fc of rock fracture of the rock based on the fractal dimension D calculated from formula (1) and formula (2) as follow:

$$F_c = D\left(1 - \frac{\alpha}{90}\right); \quad (2)$$

wherein Fc is the complexity coefficient of rock fracture; a is a fracture angle of the rock; and step E: characterizing a complexity of rock fracture of the rock based on the complexity coefficient Fc of rock fracture of the rock;

wherein the step B further comprises:

placing an end surface of the rock where the rock fracture is located within a square area of a certain length, and dividing the square area into a plurality of boxes with a side length R; and calculating the number of the square boxes N(R) containing slits in different cases by adjusting the value of the side length R;

wherein when R=R1, the number of boxes N(R) is equal to 1, and the fractal dimension D of the rock is 1; when R=R2, where R2=R1/2, the number of boxes N(R) is equal to 4, and the fractal dimension D of the rock is 2; when R=R3, where R3=R1/4, the number of boxes N(R) is equal to 16, and the fractal dimension D of the rock is 3; when R=R4, where R4=R1/8, the number of boxes N(R) is equal to 64, and the fractal dimension D of the rock is 4; and so on.

2. The method for characterizing complexity of rock fracture based on fractal dimension in claim 1, wherein the basic parameters in the step A comprise the fracture angle of the rock, Poisson's ratio, Young's modulus, peak strain, and peak stress.

3. The method for characterizing complexity of rock fracture based on fractal dimension in claim 1, wherein in the step E:

when Fc>1.2, the complexity of rock fracture of the rock is characterized as a composite failure mode;

when 1.2>Fc>1, the complexity of rock fracture of the rock is characterized as a tensile splitting mode; and when 1>Fc, the complexity of rock fracture of the rock is characterized as a shear failure mode.

4. A device for characterizing complexity of rock fracture based on fractal dimension, comprising:

a collection module, configured to collect rock fracture samples of a rock, and collect basic parameters of the rock;

a determination module, configured to determine a fractal dimension of a rock fracture morphology of the rock;

a fractal dimension calculation module, configured to calculate the fractal dimension of the rock by the formula (3) as follow;

$$N(R) = \frac{C}{R^D}; \quad (3)$$

wherein N(R) is a number of square boxes containing slits; R is a side length; D is the fractal dimension; and C is a proportional constant;

a complexity coefficient calculation module, configured to calculate a complexity coefficient Fc of rock fracture of the rock based on the fractal dimension D calculated from formula (3) and formula (4) as follow:

$$F_C = D \cdot \left(1 - \frac{\alpha}{90}\right); \quad (4)$$

wherein Fc is the complexity coefficient of rock fracture; a is a fracture angle of the rock; and a complexity characterization module, configured to characterize a complexity of rock fracture of the rock based on the complexity coefficient Fc of rock fracture of the rock;

wherein the determination module is further configured to:

place an end surface where the rock fracture is located within a square area of a certain length, and divide the square area into a plurality of boxes with a side length R; and calculate the number of the square boxes N(R) containing slits in different cases by adjusting a value of the side length R;

wherein when R=R1, the number of boxes N(R) is equal to 1, and the fractal dimension D of the rock is 1; when R=R2, where R2=R1/2, the number of boxes N(R) is equal to 4, and the fractal dimension D of the rock is 2; when R=R3, where R3=R1/4, the number of boxes N(R) is equal to 16, and the fractal dimension D of the rock is 3; when R=R4, where R4=R1/8, the number of boxes N(R) is equal to 64, and the fractal dimension D of the rock is 4; and so on.

5. The device for characterizing complexity of rock fracture based on fractal dimension in claim 4, wherein the basic parameters comprise the fracture angle of the rock, Poisson's ratio, Young's modulus, peak strain, and peak stress.

6. The device for characterizing complexity of rock fracture based on fractal dimension in claim 4, wherein:

when Fc>1.2, the complexity characterization module is configured to characterize the complexity of rock fracture of the rock as a composite failure mode;

when 1.2>Fc>1, the complexity characterization module is configured to characterize the complexity of rock fracture of the rock as a tensile splitting mode; and when 1>Fc, the complexity characterization module is configured to characterize the complexity of rock fracture of the rock as a shear failure mode.

* * * * *